United States Patent [19]

Yang

[11] Patent Number: 4,800,016

[45] Date of Patent: Jan. 24, 1989

[54] EXTRACORPOREAL BLOOD DE-HEPARINIZATION SYSTEM

[75] Inventor: Victor C. Yang, Ann Arbor, Mich.

[73] Assignee: The University of Michigan, Ann Arbor, Mich.

[21] Appl. No.: 934,012

[22] Filed: Nov. 24, 1986

[51] Int. Cl.[4] .............................................. B01D 36/02
[52] U.S. Cl. ................................ 210/206; 210/257.2;
   210/259; 210/263; 210/295; 210/321.72;
   210/502.1; 502/404; 502/401; 604/5; 424/101
[58] Field of Search ....................... 502/401, 402, 404;
   210/263, 321.3, 321.4, 502.1, 206,
   321.72–321.81, 257.2, 259, 295; 536/21;
   604/4.5; 424/101; 422/45, 101

[56] References Cited

U.S. PATENT DOCUMENTS

| | | | |
|---|---|---|---|
| 4,048,064 | 12/1977 | Clark, III | 210/638 |
| 4,175,182 | 11/1979 | Schmer | 536/21 |
| 4,198,314 | 4/1980 | Butler et al. | 502/404 |
| 4,199,502 | 4/1980 | Babson et al. | 210/690 X |
| 4,373,023 | 2/1983 | Langer et al. | 424/101 X |
| 4,381,004 | 4/1983 | Babb | 210/638 X |
| 4,464,165 | 7/1984 | Pollard, Jr. | 604/5 |
| 4,500,309 | 2/1985 | Diederich et al. | 604/5 |
| 4,551,435 | 11/1985 | Liberti et al. | 436/541 |

Primary Examiner—Richard V. Fisher
Assistant Examiner—W. Gary Jones
Attorney, Agent, or Firm—Rohm & Monsanto

[57] ABSTRACT

Heparin in an extracorporeal blood flow circuit is removed from the blood flow with the use of a filter which contains immobilized protamine on a blood-compatible support. In medical procedures where blood is processed in an extracorporeal device, such as an artificial kidney, or a heart-lung machine, the blood is heparinized to prevent clotting thereof in the channels of the extracorporeal device, and the formation of thrombi. In accordance with the invention, the processed, heparinized blood is conducted to a filter arrangement wherein protamine is held immobilized on a support formed of a blood-compatible material. Such an arrangement actually removes heparin from the blood rather than merely negates the anticoagulation effects of the heparin, as is the case in conventional protamine infusion therapy. In the present invention, the extracorporeal blood which is returned to the patient is substantially free of both heparin and protamine. Various chemical mechanisms are presented for activating a polymeric support material so as to bond covalently with the protamine.

7 Claims, 3 Drawing Sheets

EXTRACORPOREAL BLOOD DE-HEPARINIZATION SYSTEM

BACKGROUND OF THE INVENTION

This invention relates to extracorporeal blood treatment systems, and more particularly to a system wherein heparin is removed from an extracorporeal blood flow with the use of a filter arrangement containing protamine immobilized on a blood-compatible support.

It has been estimated that nearly twenty million procedures involving extracorporeal blood circulation are performed annually. Among the variety of procedures which require such extracorporeal blood flow are hemodialysis, renal transplantation, open heart operations, plasmapheresis, and blood oxygenation. Oftentimes, such procedures are of an emergency nature since, for example, patients with acute kidney dysfunction die within seven days. Functioning renal transplants have given life to tens of thousands of patients. With respect to open heart operations, also a procedure which requires extracorporeal blood treatment, the number of such procedures performed annually has been increasing by about one person per ten thousand persons per year. Currently, approximately twenty operations per ten thousand persons are performed annually. Approximately ninety thousand therapeutic plasmapheresis procedures are carried out in the United States. The artificial lung, also known as the blood oxygenator, has become an essential life saving device used to treat patients suffering from acute respiratory failure and infants with diaphragmatic hernia. In addition to the foregoing, it is expected that new procedures which are presently in the conceptual stage, such as the implantation of artificial livers and artificial hearts will increase the number of procedures which require extracorporeal circulation.

In all of the procedures mentioned hereinabove, blood is drawn from a patient and passed through an extracorporeal device. It is a problem with such systems, however, that upon contact with the synthetic materials which form the surfaces of the extracorporeal devices, the blood's precisely regulated hemostasis is disturbed, and therefore the blood tends to clot within the device. The thrombi which are formed occlude the perfusion channels in the device. Presently, occlusion is prevented and fluid it maintained in extracorporeal circulation by the use of heparin, which is the most widely used anticoagulant. The heparin is systemically administered to the patient and the extracorporeal device prior to treatment. However, the high level of heparin required for the purpose poses a considerable hemorrhagic hazard to the patients. It has been reported that eight to thirty percent of all hemorrhagic complications occur during heparinization. Additionally, a six to ten percent incidence of coagulation abnormalities with excessive post-operative bleeding is reported in patients who have undergone open heart surgery. In patients who have a high risk of hemorrhage, bleeding complications occurred in ten percent of those who received low dose heparin treatment, and nineteen percent of those receiving regional heparin anticoagulation. It has been further estimated that nearly twenty five percent of all patients suffering from acute renal failure were subject to increased bleeding risk during and immediately following dialysis. Such complications are enhanced for elderly patients, patients with ulcers or other multiple traumata, and patients who recently have undergone cardiac or vascular surgery.

In addition to hemorrhage, there are a variety of other complications associated with heparinization, particularly when the drug is administered over a long period. These additional complications include thrombocytopenia, alopecia, arterial embolus anaphylaxis, and interference with bone repair and maintenance. It is therefore significant that heparin has been cited as the drug responsible for the majority of drug deaths in patients who are reasonably healthy.

As a result of the life-threatening nature of the hemorrhage associated with systemic heparinization, considerable effort has been directed at solving this problem. One general approach which is widely and commonly used in clinical practice includes the administration of anti-heparin compounds, such as protamine, to neutralize the anticoagulant effects of heparin. Another approach to this problem in the prior art is the development of heparin substitutes, such as prostacyclin, and new antithrombotic agents, such as low molecular weight heparins. A still further prior art approach to this problem involves the use of low-dose heparinization, or regional anticoagulation, by infusion of heparin into the blood entering the dialyzer, and subsequent neutralization of the heparin by infusion of protamine into the heparinized blood as it returns to the patient. It is also known to use regional citrate anticoagulation, in a manner similar to that discussed hereinabove, except that citrate is used as the anticoagulant agent, and calcium is used as the neutralizing agent.

One recent approach to the problem of reducing blood clotting within extracorporeal devices involves the development of new blood compatible materials with surface bound heparin for construction of the extracorporeal devices. This approach, however, requires that the entire extracorporeal unit be made of such materials, otherwise clotting will still occur in the devices. It is almost impossible to construct the entire extracorporeal unit using such materials.

A still further prior art approach to the aforementioned clotting problem involves the development of an immobilized heparinase filter to degrade heparin at the termination of extracorporeal circulation. Heparinase is an enzyme which degrades heparin specifically into relatively inactive low molecular weight fragments, and can be used to neutralize the anticoagulant effects of heparin. Heparinase is a microbial enzyme, and use of such enzymes can lead to acute or chronic immunological responses. In addition, as are most enzymes, heparinase is unstable and loses its enzymatic activity easily under physical and chemical processing. The instability of the heparinase molecule has been shown to limit the methods which can be used to immobilize the heparinase as well as the materials which can be used as biocompatible supports. Thus, the use of heparinase limits the efficiency of the reactor during in vivo operations. In addition to the foregoing, it is extremely difficult to sterilize or to store the heparinase based enzyme reactor without suffering significant loss of the enzyme's catalytic activity. The accumulation in the body of a patient of unnatural heparin degradation products resulting from the reaction of a heparinase reactor may also pose a serious toxic threat. This is particularly disturbing in view of the fact that heparinase molecules, though covalently attached to the support material, can be slowly but continuously leached off of the support materials. It is therefore of great concern that even trace amounts of the microbial enzyme would trigger untoward immunological responses.

It stands to reason that none of the aforementioned approaches to the problem of extracorporeal clotting have met with much clinical success. For example, direct intravenous administration of protamine has been reported widely to induce serious (or even fatal) anaphylactic response. Prostacyclin infusion is associated with the unpredictable occurrence of sudden hypotension. The use of low molecular weight heparins as new anti-thrombotic agents has been restricted due to the lack of neutrailizing agents for these compounds. The use of low-dose heparinization or regional heparin anticoagulation has proved unsuccessful in preventing bleeding associated with dialysis. Moreover, regional heparin anti-coagulation does not obviate the need for protamine as the neutralizing agent. Regional citrate anticoagulation is rarely used because of the technical difficulties in performing the procedures and in determining the adequate amount of calcium required for citrate neutralization.

It is therefore, an ooject of this invention to provide a simple, economical and effective system for removing extracorporeal heparin.

It is also an object of this invention to prevent clotting when extracorporeal blood communicates with extracorporeal devices, without introducing heparin into the living being.

It is another object of this invention to reduce the possibility of hemorrhagic and other complications associated with the use of heparin.

It is a further object of this invention to eliminate the effects of heparin without introducing protamine into the living being.

It is additionally an object of this invention to remove heparin from extracorporeal blood with the use of protamine.

It is yet another object of this invention to prevent the toxic effects of protamine resulting from heparin neutralization with protamine.

It is a still further object of this invention to produce a heparin removal system which can be easily sterilized.

It is an additional object of this invention to provide a heparin removal system wherein the heparin neutralization agent is stable.

It is still another object of this invention to provide a heparin removal system which will not trigger immunological responses in living beings.

It is a yet further object of this invention to produce a heparin removal system which will not produce foreign degradation products.

It is also another object of this invention to provide an anticoagulation system which removes heparin from extracorporeal blood, rather than merely neutralize its effects.

SUMMARY OF THE INVENTION

The foregoing and other objects are achieved by this invention which provides an extracorporeal apparatus for treating a blood fluid, the apparatus having an inlet for receiving blood to which has been added heparin. In accordance with the invention, protamine is immobilized on a blood-compatiole support and arranged to communicate with the heparinized biood fluid. Such communication results in the removal of the heparin from the blood fluid.

In accordance with one aspect of the invention, the deheparinization system is used in combination with a further extra-corporeal device, such as an artificial kidney or an artificial heart-lung device. Preferably, heparin is added to the flow of blood fluid which is conducted to the extracorporeal device, and thereby prevents coagulation and the generation of thrombi in the channels of the extracorporeal device. The treated blood fluid, which contains heparin, is then conducted to the subject deheparinization system wherein heparin is removed and the blood fluid is returned to the living being essentially free of heparin and free of protamine. Thus, the need for infusion of protamine into the living being, and the dangers resulting therefrom, are eiiminated.

As indicated, protamine is held immobilized on a blood-compatible support, illustratively by covalent bonding. In certain embodiments, the blood-compatible support may be a polymer support matrix which may have on a surface thereof a substantial number of reactive functional groups, such as hydroxyl, amino or carboxyl groups, which can be activated for bonding with protamine. Such a polymer support matrix may include ethylene vinyl alcohol, nylon, or polyurethane. The blood-compatible support may aiso comprise regenerated cellulose hollow fibers.

It is a feature of the present invention that the subject filter allows for regional heparinization, as compared to regional anticoagulation, because it actually removes heparin from the blood fluid rather than just neutralizes heparin's anticoagulant effects. This serves to limit heparin's toxic effects. Additionally, the present invention permits the use of higher heparin concentrations in the extracorporeal devices so as to extend the operational lifetimes of such devices.

It is to be noted that the preparation of an immobilized protamine filter requires careful selection of the support matrix. A prerequisite for the support material is that it must be biocompatible and must contain the necessary functional groups to allow protamine to be bound covalently to the support material. Preferably, the support material must be stable and not be chemically or enzymatically degraded by blood, have good flow characteristics and sufficient mechanical strength and durability to withstand long-term high operating pressures encountered in extracorporeal circulation, and be blood-compatible. With respect to the requirement of blood-compatibility, the support material must not cause hemolysis and undue platelet binding, thrombus formation, the activation and damage of blood components, and toxicity. Although there is not yet known a material which fulfills all of the foregoing requirements in an ideal sense, particularly with regard to blood compatibility and mechanical durability, good compromises can be found in the biomaterials which have been used to construct the extracorporeal devices currently on the market. As will be described hereinbelow, various procedures can be applied to activate these known materials to produce an extracorporeal de-heparinization apparatus.

BRIEF DESCRIPTION OF THE DRAWING

Comprehension of the invention is facilitated by reading the following detailed description in conjunction with the annexed drawing, in which.

DETAILED DESCRIPTION

Figure 1:
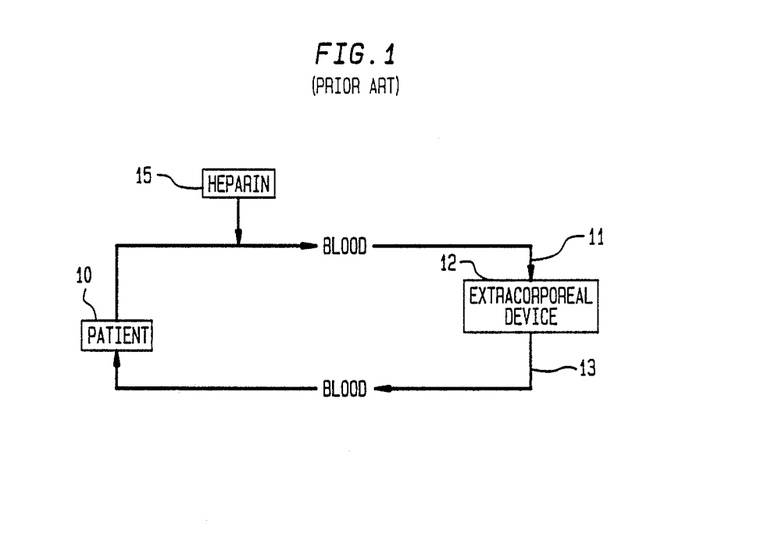
FIG. 1 is a schematic representation of a prior art circuit for extracorporeal blood circulation.

FIG. 1 is a schematic representation of an extracorporeal blood flow circuit as used in the prior art. More specifically, the blood of a patient 10 is conducted to an inlet 11 of an extracorporeal device 12. Circulation is completed by returning the blood from an outlet 13 of the extracorporeal device to patient 10. In this known arrangement, the patient's blood is heparinized by the infusion of heparin at a heparin inlet 15. The heparin is shown to be added prior to extracorporeal device 12 and can be administered either systemically to the patient or continuously infused into the blood after it is drawn from the patient. Thus, the blood which is returned to the patient contains heparin. In some known arrangements, protamine may be added to the returning blood or given to the patient systemically following treatment to nullify the anticoagulating effects of the heparin.

Figure 2:
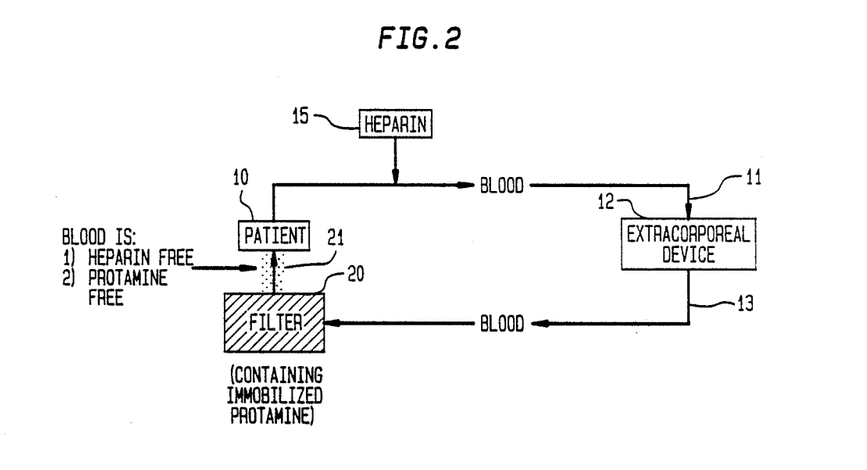
FIG. 2 is a schematic representation of a circuit employing the principles of the present invention for extracorporeal blood circulation.

FIG. 2 is a schematic representation of an extracorporeal blood circulation system employing the present invention. In this specific embodiment, the blood of patient 10 is heparinized via a heparin inlet 15 prior to it being received at inlet 11 of extracorporeal device 12. This portion of the blood flow circuit is therefore similar to that described hereinabove with respect to FIG. 1. However, in accordance with the invention, a filter arrangement 20 is provided interposed in the extracorporeal blood flow between outlet 13 of the extracorporeal device and the patient As will be described in greater detail hereinbelow, filter 20 is arranged to contain immobilized protamine (not shown) which removes the heparin from the returning blood. In addition, since the protamine is immobilized, the blood which actually returns to the patient from an outlet 21 of the filter is both heparin and protamine free.

It is, thus, an important feature and advantage of this invention that the patient is never subjected to either heparin or protamine during the course of an extracorporeal therapy procedure. The filter arrangement of the instant invention allows for regional heparinization of blood only in the extracorporeal device and regional protamine treatment of blood only in the filter arrangement. The entire process takes place external to the body and the blood is returned to the body in a substantially normal state thereby reducing the hemorrhagic risks associated with heparin administration and the toxic effects of protamine administration.

The terminology "filter arrangement" has been used herein to illustrate an application of the novel de-heparinization system. This filter arrangement may comprise a blood filter, such as the FDA approved Bently AF-1025 arterial blood filter, containing a biomaterial such as sephadex, sepharose, cellulose or polyurethane particles having protamine immobilized thereon. The terminology "filter arrangement" should be construed broadly to indicate any means of "filtering", i.e., removing and retaining, unwanted protamine and heparin from the blood fluid prior to re-entry into the body of the patient. Other examples, therefore, would include protamine immobilized on a line of tubing in the system, such as nylon or polycarbonate tubing, or protamine immobilized directly on hemofilter or hemodialyzer equipment.

As discussed hereinabove, the major criterion for choice of a support material for the filter arrangement is that it be biocompatible. Moreover, the support material should have reactive functional groups, such as hydroxyl groups, amino groups, carboxyl groups, etc., which will chemically bind protamine, or which can be activated to bind protamine. For the purpose of illustrating application of this invention, some materials commonly used in the manufacture of extracorporeal blood treatment devices have been suggested as support materials and methods of binding protamine to them are given below in the illustrative examples relating to FIGS. 3-5.

It should be noted, however, that other biomaterials, such as polysulfone, polycarbonate, polyether, or polyethercarbonate, or biomaterials yet to be discovered and/or developed could be utilized in the novel de-heparinization system described herein. In addition to the specific illustrative examples described hereinbelow, a variety of activation methods and coupling procedures can be employed to immobilize the protamine. Reference to the following texts should enable one of ordinary skill in the art to devise alternative methods: I. Chibata, *Immobilized Enzymes*, Halstead Press, N.Y. (1978) and K. Mosbach, "Immobilized Enzymes," *Methods in Enzymology*, Vol. 44 (1976).

Figure 3:
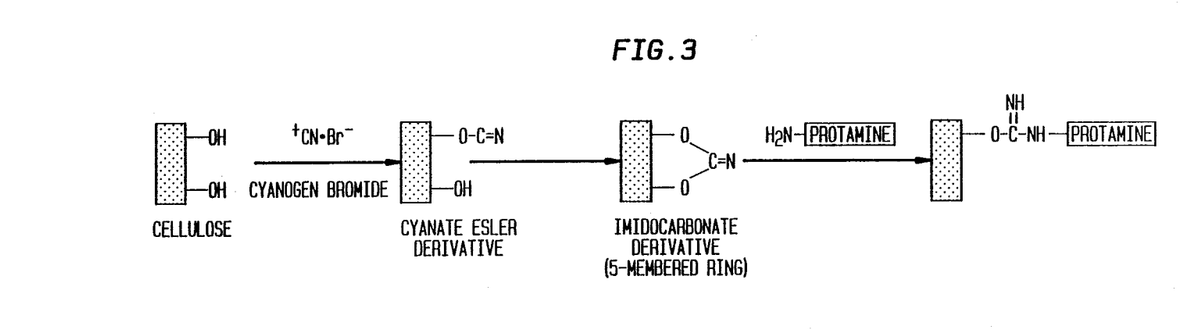
FIG. 3 is a representation of a process for activating a cellulose support and coupling protamine thereto.

FIG. 3 is a representation of chemical reactions used in activating a support made of cellulose, and the coupling of protamine thereto. In this specific embodiment, the cellulose support material is a regenerated cellulose hollow fiber which has been used in the construction of hemodialyzers. As shown in the figure, the cellulose material contains abundant hydroxyl groups on the surface thereof which can be activated with cyanogen bromide. In a specific illustrative example, small hollow fiber bundles which consist of approximately 175 regenerated cellulose fibers of approximately 10 cm in length are used. These fibers are introduced into a housing (not shown), potted, closed by end caps (not shown), and then sealed by ultrasound. The cellulose fibers are activated by soaking the bundle of such fibers in 50 ml of 1M sodium carbonate solution for 5 minutes. The bundle is subsequently washed with 100 ml of the same sodium carbonate solution. While the bundle is vigorously agitated in a fume hood (not shown), 50 ml of CNBr/acetonitrile solution (lg/ml) is passed through the bundle over a period of approximately 5 minutes. To achieve protamine coupling, the bundle is washed with distilled water, 1 mM HCl, and 0.1M NaHCO$_3$ buffer (pH 8.3) containing 0.5M Nacl. Protamine solution (10–100 mg/ml in 0.1M NaHCO$_3$, 0.5M NaCl, pH 8.3) is then circulated through the bundle at a flow rate of 5 ml/min over a period of approximately three hours at room temperature. The mechanism of the activation of the support and the coupling of the protamine on the support is shown in this figure.

A further material, ethylene vinyl alcohol, which is commonly used in a hemodialyzer, can also be used in the practice of the invention. Like regenerated cellulose, this material contains abundant hydroxyl groups and can be activated by cyanogen bromide. Thus, the material can be activated and the protamine immobilized thereon in a manner similar to that described hereinabove with respect to the cellulose hollow fiber support material.

Figure 4:
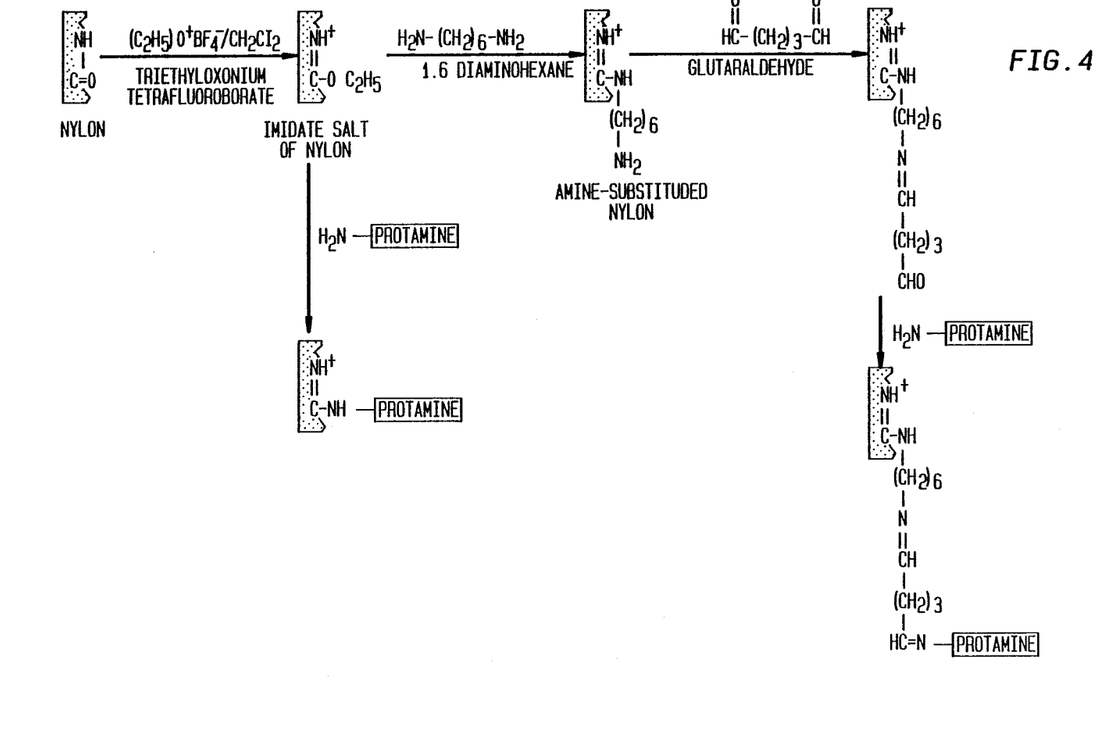
FIG. 4 is a representation of a process for activating a nylon support member and coupling protamine thereto.

FIG. 4 is a representation of the chemical mechanisms involved in activating a nylon support material, and immobilizing protamine thereon. Nylon is readily available in a wide variety of physical forms, such as films, membranes, and tubes. Many of these forms are routinely encountered in extracorporeal blood circulation. Native nylon of high molecular weight has few end groups, and therefore must be pretreated in order to generate potentially reactive groups which are capable of interacting covalently with protamine molecules. Many methods are known for generating reactive groups on the nylon.

The simplest method of generating reactive groups in nylon includes hydrolytic cleavage of the nylon with strong acid to create reactive centers, mainly aliphatic amino and carboxyl groups. However, this method is not quite satisfactory, since it involves partial depolymerization of the nylon which may lead to impairment of the mechanical strength of the support. The method shown in FIG. 4 employs treatment of the nylon with triethyloxonium tetrafluoroborate to generate the reactive centers. This method permits the reactive groups to be generated without necessitating any depolymerization of the support.

In a specific illustrative example, a 3-meter length of nylon tube is filled with triethyloxonium tetrafluoroborate solution (10% w/v in dry dichloromethane) and incubated at room temperature for approximately 15 minutes. The tube is then washed through for approximately two minutes with dichloromethane and for two minutes with dioxane. Immediately after the dioxane wash, the tube is filled with 1,6-diaminohexane solution (10% w/v in methanol), incubated at room temperature for approximately three hours, and then treated with 5% (w/v) glutaraldehyde in 0.2M borate buffer (pH 8.5) for approximately 20 minutes at room temperature. For protamine immobilization, the tube is washed thoroughly with 0.1M phosphate buffer (pH 8.0) containing 0.5M NaCl, and incubated with protamine solution (10–100 mg/m: prepared in the same phosphate buffer) for approximately two hours at room temperature.

Figure 5:
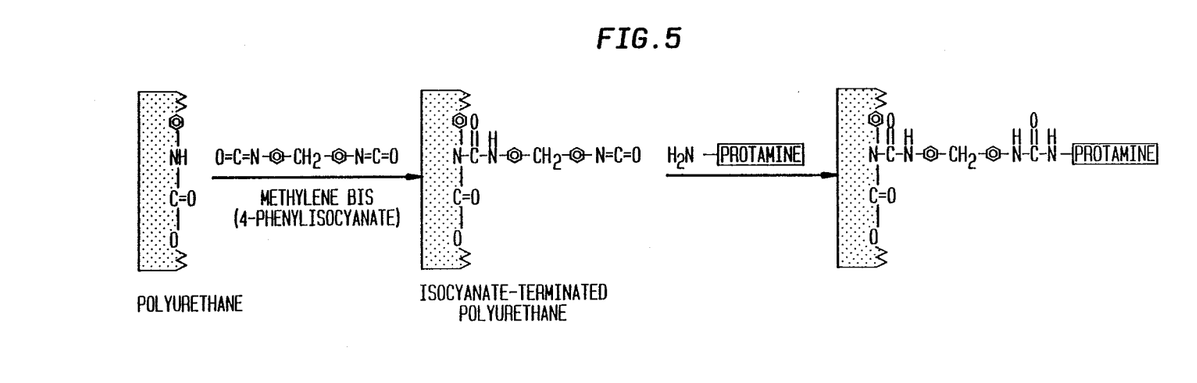
FIG. 5 is a representation of a process for activating a polyurethane support member and coupling protamine thereto.

FIG. 5 is a representation of the chemical mechanisms involved in activating polyurethane support material and immobilizing protamine thereon. In a specific illustrative example, a ten $cm^2$ Pellathane sheet (available from Upjohn) is soaked in toluene for approximately ten minutes to remove surface impurities. After soaking, the support material is placed in 50 ml of 0.25M methylenebis (4-phenylisocyanate) in trimethylpentane under dry nitrogen, and incubated at approximately 80 degress C. for one hour with gentle agitation. For protamine immobilization, the activated support material is washed with ethanol and distilled water, and placed in the protamine solution (10–100 mg/ml in physiological saline buffer, pH 7.4) for approximately one hour.

Protamine is a low molecular weight protein rich in lysine, arginine, and other basic amino acids. Owing to a strong net basic charge, protamine interacts with sulfate groups on heparin, forming a tightly bound complex by electrostatic interaction thereby neutralizing the effect of heparin. Several experiments were conducted to demonstrate that bound protamine operates as effectively as free protamine to neutralize heparin.

Protamine was immobilized on cyanogen bromide-activated 8% cross-linked agarose beads in accordance with the methods described hereinabove. Although agarose is not considered to be a blood-compatible material, and therefore is unacceptable as a support, the experiments did demonstrate that immobilized protamine behaves substantially the same as free protamine. One ml of the suspended agarose beads (75% suspension in physiological saline solution) containing 12.3 mg of protamine per ml of the beads was mixed with 9 ml of citrated normal human plasma in the presence of 500 units of heparin. The mixture was incubated at 37° C. with gentle agitation for 3 min, and the beads were removed by centrifugation. Heparin concentration in the supernatant was then measured by two known assays, the APTT clotting assay and the anti-FXa amidolytic assay. An identical experiment was conducted for a control sample which consisted of agarose beads with no protamine bound to them. In contrast to the control sample, more than 95% of both APPT and i-FXa activities were removed in the test sample after the treatment with immobilized protamine.

In vitro experiments showed that 0.01 ml of cross-linked agarose beads containing 8 mg of protamine per ml of the beads removed 20 units of heparin in a single operation. In vivo experiments using sheep as the animal model showed that a Bentley AF-1025 blood filter containing 75 ml of agarose beads with an immobilized protamine concentration of 50 mg/ml of beads attached at the effluent of an extracorporeal circuit could remove 60–75% of administered heparin in a single passage. The animal used for these experiments was heparinized with an initial dose of 5,000 units of heparin, followed by continuous infusion of 20,000 units of heparin. only minor blood damage was found at the end of the experiments, as indicated by the white blood cell counts, red blood cell counts and platelet counts in the blood samples drawn from the animal.

Although the invention has been described in terms of specific embodiments and applications, persons skilled in the art can, in light of this teaching, generate additional embodiments without exceeding the scope or departing from the spirit of the claimed invention, as in evident, the novel deheparinization system can be applied to a wide variety of situations such as hemodiolysis, hemofiltration, extracorporeal membrane oxygenation, open heart surgery, plasmapheresis, etc. accordingly it is to be understood that the drawing and description in this disclosure are proffered to facilitate comprehension of the invention and should not be construed to limit the scope thereof.

What is claimed is:

1. A system for extracorporeal treatment of blood of a living in an extracorporeal device having an inlet and an outlet, the system comprising;
    means for adding heparin to an extracorporeal flow of the blood prior to the blood entering the inlet of the extracorporeal device; and
    filter means formed of protamine for binding said heparin, said protamine being immobilized in a biocompatible polymer support material, said filter means being coupled to the outlet of the extracorporeal device prior to returning the blood to a living being, whereby the returned blood is substantially free of said heparin.

2. The system of claim 1 wherein said protamine is covalently bound to said polymer support matrix.

3. The system of claim 1 wherein said polymer support matrix is characterized by having reactive functional groups on a surface thereof.

4. The system of claim 3 wherein said reactive functional groups are selected from the group consisting of hydroxyl groups, amino group, and carboxyl groups.

5. The system of claim 1 wherein said biocompatible support matrix is selected from the group consisting of cellulose, ethylene vinyl alcohol, nylon, ployurethane, polysulfone, polycarbonate, polyether, and polyethercarbonate, 6. An extracorporeal apparatus for treating a blood fluid, the apparatus comprising:
   inlet means for receiving a heparinized blood fluid;
   support means formed of a blood-compatible material and having protamine immobilized thereon for communicating with and removing haepain from the blood fluid;
   means for returning the blood fluid, withour the removed heparin, to a living being; and
   an artificial kidney for operating on the blood fluid, said artificial kidney having an outlet coupled to said inlet means.

7. An extracorporeal apparatus for treating a blood fluid, the apparatus comprising:
   inlet means for receiving a heparinized blood fluid;
   support means formed of a blood-compatible material and having protamine immobilized thereon for communicating with and removing heparin from the blood fluid;
   means fro returning the blood fluid, without the removed heparin, to a living being; and
   an artificial heart-lung for operating on the blood fluid, said artificial lung having an outlet coupled to said inlet means.

* * * * *

UNITED STATES PATENT AND TRADEMARK OFFICE
CERTIFICATE OF CORRECTION

PATENT NO. : 4,800,016
DATED : January 24, 1989
INVENTOR(S) : Victor C. Yang

Page 1 of 2

It is certified that error appears in the above-identified patent and that said Letters Patent is hereby corrected as shown below:

Column 1, between the title and the heading "Background of the Invention", please insert the following paragraph:

-- Government Rights

This invention was made with Government support under Grant No. HL38353 awarded by the National Institutes of Health. The Government has certain rights in the invention.--

Column 1, line 48, change "it " to -- is --;
Column 3, line 23, change "ooject" to -- object --;
Column 3, line 65, change "blood- compatiole" to -- blood-compatible--;
Column 4, line 14, change "eiimiinated" to -- eliminated--;
Column 4, line 26, change "aiso" to -- also --;
Column 5, line 42, after "patient" insert -- . --;
Column 7, line 45, change "mg/m:" to -- mg/ml --;
Column 7, line 56, change "degress" to -- degrees --;
Column 8, line 12, change "C." to -- C --;
Column 8, line 16, change "APTT" to -- APPT --;
Column 8, line 21, change "i-FXa" to -- anti-FXa --;
Column 8, line 34, change "only" to -- Only --;

UNITED STATES PATENT AND TRADEMARK OFFICE
CERTIFICATE OF CORRECTION

PATENT NO. : 4,800,016

DATED : January 24, 1989

INVENTOR(S) : Victor C. Yang

It is certified that error appears in the above-identified patent and that said Letters Patent is hereby corrected as shown below:

Column 8, line 44, change ", as in" to -- . As is --;

Column 8, line 48, change "accordingly" to --Accordingly,--;

Col. 8, Claim 1, line 2, after "living" insert --being--;

Col. 8, Claim 1, line 3, change ";" to --:--;

Col. 9, Claim 4, line 3, change "group" to --groups--;

Col. 9, Claim 5, line 3, change "ployurethane" to --polyurethane--;

Col. 9, Claim 5, line 5, change "," to --.--;

Col. 9, Claim 6, line 6, change "haepain" to --heparin--;

Col. 9, Claim 6, line 8, change "withour" to --without--; and

Col. 10, Claim 7, line 8, change "fro" to --for--.

Signed and Sealed this

Twenty-second Day of December, 1992

*Attest:*

DOUGLAS B. COMER

*Attesting Officer*   Acting Commissioner of Patents and Trademarks